United States Patent [19]
Holmgren

[11] Patent Number: 5,598,185
[45] Date of Patent: Jan. 28, 1997

[54] SYSTEM FOR ANALYZING MEDICAL IMAGES HAVING A PARTICULAR COLOR AND INTENSITY LOOK-UP TABLE

[75] Inventor: Bengt G. Holmgren, New York, N.Y.

[73] Assignee: Integrated Image Solutions, Farmingdale, N.Y.

[21] Appl. No.: 258,059

[22] Filed: Jun. 10, 1994

[51] Int. Cl.⁶ .......................... G06F 159/00; G09G 5/04; G06K 9/00
[52] U.S. Cl. .......................... 345/153; 345/147; 345/199; 395/131; 395/132; 382/132; 382/162; 128/630
[58] Field of Search ........................ 364/413.22, 413.13, 364/413.14; 382/6, 41, 54–56, 162, 164, 128, 165, 132; 348/25, 26, 27, 28, 29, 30; 395/126, 129, 131, 132; 128/630; 345/147, 150, 153, 199

[56] References Cited

U.S. PATENT DOCUMENTS

| | | |
|---|---|---|
| 4,340,911 | 7/1982 | Kato et al. . |
| 4,697,594 | 10/1987 | Mayo, Jr. . |
| 4,868,651 | 9/1989 | Chou et al. . |
| 4,991,092 | 2/1991 | Greensite ......................... 364/413.13 |
| 5,063,583 | 11/1991 | Galkin . |
| 5,172,419 | 12/1992 | Manian . |
| 5,212,637 | 5/1993 | Saxena . |

*Primary Examiner*—Robert A. Weinhardt
*Assistant Examiner*—Joseph Thomas
*Attorney, Agent, or Firm*—Pollock, Vande Sande & Priddy

[57] ABSTRACT

A procedure and device for analyzing the gray scale of mammograms. Mammogram images are digitized and subject to image enhancement by manipulating the gray scale. Each pixel of the digitized mammogram is grouped as to a gray scale interval and those pixels lying in the same gray scale interval are assigned a common display value. The display values are displayed for each pixel location on both a color and monochrome monitor producing a unique pattern giving a finer detailed image of density changes in breast parenchyma. Interpretation of these patterns indicate suspicious areas where immediate magnification of the suspect area can produce a better image of a mass for application of known malignant tumor characteristics.

6 Claims, 5 Drawing Sheets

SYSTEM FOR ANALYZING MEDICAL IMAGES HAVING A PARTICULAR COLOR AND INTENSITY LOOK-UP TABLE

The present invention relates to a device for analyzing medical diagnostic images. Specifically, an apparatus and method are provided for analyzing black and white mammographic films to detect changes in tissue densities which may signify a suspicious lesion.

Mammograms are an x-ray recording of the breast with high spatial resolution and good contrast separation depicting different tissue densities as the photons pass through the breast displaying the densities in a full range of gray scale from black to white with the densest tissue being pure white to the human eye and the least dense tissue as black. The mammogram is reviewed while supported over a light box to facilitate "reading" them. Reading them entails a complex series of evaluations on behalf of a radiologist aided only with a magnifying glass to determine if the densities are of a suspicious nature. A suspicious density or mass detected by a radiologist would then be recommended for biopsy and verification by a pathologist before it is considered cancerous and excised.

Early detection of cancer requires proper diagnoses and treatment of a suspicious lesion at the earliest possible stage. A suspicious lesion/malignancy is indicated on the x-ray by any number of factors including asymmetry, architectural distortion and neodensity, calcifications, and masses.

The earliest a cancer can be distinguished by the human eye on a mammogram is when it has been growing in the body for approximately 5–7 years. Anything less than this (at this time) is considered a serendipitous finding. Consequently, dangerous malignant conditions may go undetected until such time as a density change in the tissue is visible to the human eye.

The problem of early detection is compounded by the fact that the amount of X-ray dosage received by a patient must be limited. Too frequent examinations and/or many magnification views of suspicious areas in the breast present a danger of overexposure to X-ray radiation. Consequently, it is recommended that women 50 and over, or in a high risk category, space their mammograms a year apart. Carcinomas which go undetected in an earlier mammogram, may significantly progress undetected until they can be seen by the radiologist before the next scheduled mammogram is produced.

The current mode of detecting malignancies on a mammogram is to actually see a suspicious lesion with the human eye aided only by the magnification of a hand-held magnifying glass. The mass has to be large enough or prominent enough to be seen by crude methods available today, thereby creating a time lapse of years between the carcinoma's inception to detection.

In order for the human eye to more readily "see" the malignancy, current x-ray techniques increase the crispness of the image on the film by increasing contrast; thereby, eliminating much of the "extraneous" gray area that has heretofore been deemed inconsequential. The concept of digitizing a mammogram to achieve better contrast is described e.g. in U.S. Pat. No. 4,340,911 and in U.S. Pat. No. 5,212,637 which attempts to automatically find tissue calcifications. The use of pseudo colors to enhance X-ray images by this invention has been found to be most useful and necessary in aiding radiologists to read mammograms. With the advent of this invention in analyzing and displaying 256 shades of gray in a cohesive and cogent unique manner, subtle changes in surrounding tissue are now being seen and recognized for their key to identifying early changes occurring in the breast tissue which facilitates the identification of a precursor of cancer for the first time.

Image analyses which identify suspicious tissue in the earliest stages of a malignancy would make an earlier diagnosis possible increasing still further the survival rate of cancer victims.

SUMMARY OF THE INVENTION

It is an object of this invention to detect changes in tissue density represented in a mammogram.

It is a further object of this invention to detect and display the prerecognizable malignant condition of surrounding tissue through an image analysis of tissue density changes in a mammogram.

It is yet another object of this invention to display stress/distortion patterns contained in human tissue which precede the visibility of carcinomas in breast parenchyma.

It is yet another object of this invention to permit the radiologist the ability to enlarge specific areas of the mammogram without exposing the patient to additional radiation.

These and other objects of the invention are provided by a system which performs an analysis on a digitized video image of human tissue. The video image may be produced from a mammogram and comprises a frame of pixels which is stored in a memory. The stored pixels have a gray scale value representing the tissue density at discreet locations on the medical image.

Areas of tissue stress are located in accordance with the invention by translating the gray scale of a pixel into one of a limited number of discreet gray scale values. Pixels having gray scale values which lie within a small interval are translated into the same new gray scale, thus forming bands of gray scale. Each new gray scale level of a pixel is displayed on a monochrome monitor, and is preferably translated into a color and displayed on a color monitor. Areas of constant density are displayed as contours having the same display value. Areas of high tissue stress which define an area of a suspicious lesion produce a tissue density gradient which will be displayed as several adjacent bands or contours of gray scale having a distinctive shape. Tension forces in the tissue which produce the gradient tend to emanate from a region developing a malignant tumor before it is otherwise detectable.

In accordance with a preferred embodiment of the invention, each new gray scale value is assigned a color. As such the boundaries between the intervals of gray scale levels, representing a subtle tissue density gradient are identified by the boundary between displayed colors.

In carrying out the invention in accordance with the preferred embodiment, the various gray scale intervals may be changed by adjusting the brightness on the camera, thereby changing the boundaries between intervals to emphasize gray scale changes of the video image. The information is displayed such that changes in density are emphasized to locate areas of high stress, thus leading to an early detection of suspicious tissue.

THE DESCRIPTION OF THE FIGURES

DESCRIPTION OF THE PREFERRED EMBODIMENT

Figure 1:
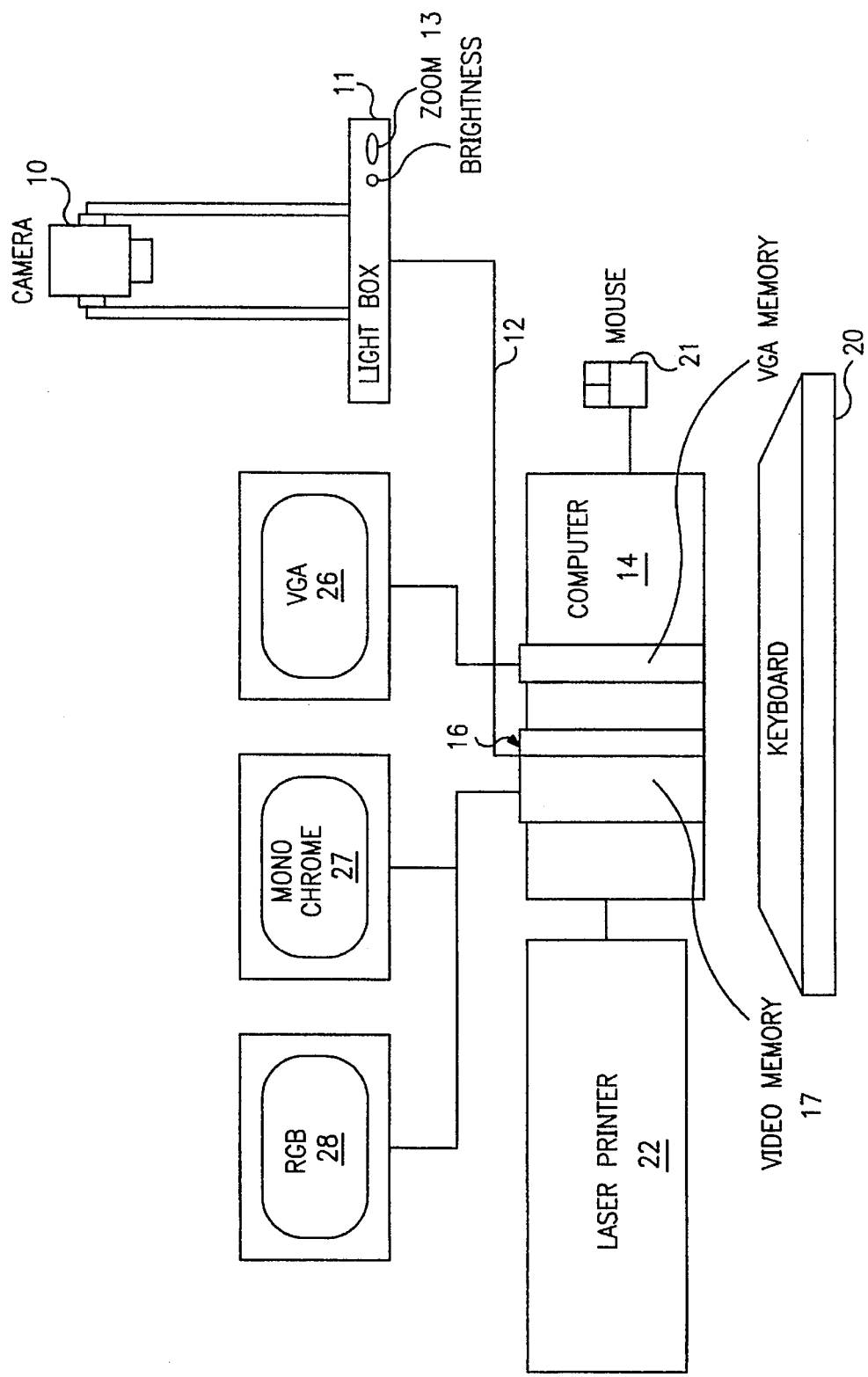
FIG. 1 illustrates the system configuration for the preferred embodiment of the invention.

Referring now to FIG. 1 there is shown a system for digitizing mammogram photographs, and displaying an enhanced digitized mammogram image. The system includes a camera 10 which is a video scanning camera. The camera 10 is positioned vertically above a light box 11, which supports and illuminates a mammogram under examination. The camera 10 produces the video signal 12, for digitization by an analog to digital card 16 installed within a slot of the computer 14. The computer 14 may be a standard 486SX-66, programmed in accordance with the program depicted in the flow charts of FIGS. 4 and 5.

The system of FIG. 1 has three monitors associated with it. VGA monitor 26 displays the program menus for the software in computer 14. A monochrome monitor 27 and standard RGB color monitor 28 are provided to display the digitized image representing the scanned mammogram.

Although the preferred embodiment is directed to scanning and producing images from back-lighted mammograms for analysis, it is clear that other sources of images, i.e. direct x-ray detection output, ultrasonic detection systems, and other medical imaging devices may provide the video image signal for display and analysis in accordance with the principles of the invention.

The keyboard 20 and mouse 21, for computer 14 permit the operator to enter various commands in response to the menu driven software of computer 14. A laser printer 22 produces a hard copy of the images displayed on the monochrome monitor 27 and RGB color monitor 28.

A video signal generator on the video memory board 17 generates a video signal from the digitized image pixels. Monochrome and color monitors 27 and 28 produce an image display from the video signal.

Additionally camera 10 can do image enhancement by the usual zoom command, initiated by a local control function 13 permitting inspection of localized area of the mammogram in greater detail.

Figure 2:
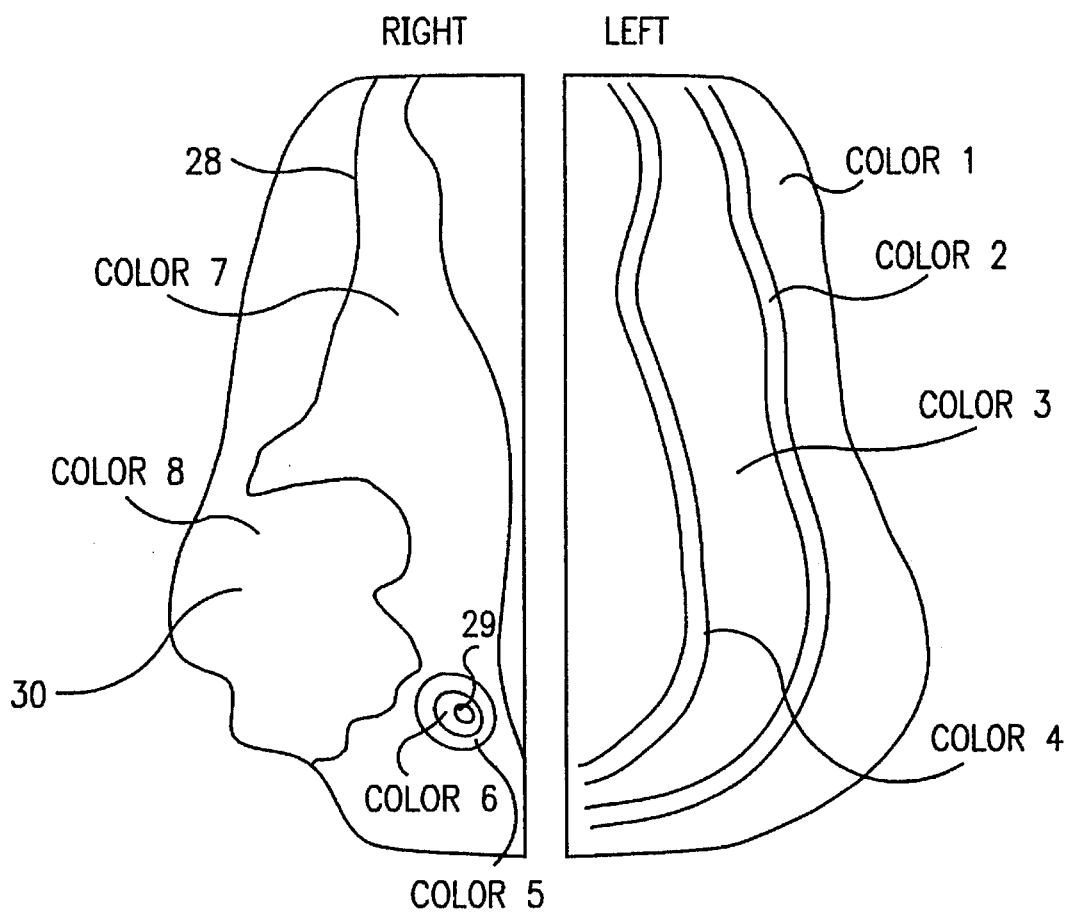
FIG. 2 illustrates the identification of high tissue stress areas of an image in accordance with the preferred embodiment of the invention.

FIG. 2 illustrates a typical digitized image pattern, processed in accordance with the present invention which will permit the identification of the early stages of calcification in breast tissue. The illustrated mammogram of FIG. 2 contains a mediolateral view of the right and left breasts, taken from the same angle and position. The left, normal breast shows regular contours of constant density depicted by colors 1–4, which tend to follow the breast profile. The right breast shows a dark spot in the area indicated by 29. To the left of the smaller dark spot, a much larger dark area 30 is defined, bounded by the distinct light boundary of color 7. The contours of constant density have a unique shape from tension induced in the tissue by the malignancy.

It has been observed in accordance with the preferred embodiment of the invention that the first smaller area 29 represents the malignancy, whereas the larger area 30 represents tissue density change, due to tension forces impacting on the surrounding tissue from the smaller malignant area 29. The highly subtle tissue density changes are not perceivable by the naked eye of a radiologist Or clinician (or even with a magnifying glass), when viewing the illuminated mammogram.

The present invention can distinguish subtle transitions (gradients) in gray scale which accompanies stress induced in the tissue from the growing carcinoma. The larger tissue area 30 containing stress lines, all of which would appear to emanate from the center of the malignancy are only seen when processing of the digital image data is effected in accordance with the present invention.

Tissue density changes which skilled clinicians can analyze are highlighted by the invention which represents small gray scale intervals by different colors 5–8. Once these changes in tissue density levels, which may be very subtle, are identified, the original mammogram can be examined in greater detail in the areas effected to determine the cause of the tissue density gradient.

As is known, the pixel values stored in the video memory board 17 of FIG. 1 comprise one of (for example) 256 gray scale levels. The number of discreet gray scale levels depends upon the digitizer resolution.

The 256 levels of gray scale, are divided up into discreet intervals. These discreet intervals represent separate contiguous ranges of gray scale, and pixels having a gray scale lying within the interval are displayed with a color, by RGB monitor 28. In the case of the monochrome monitor 27, pixels having a gray scale within the same interval are displayed with the same gray scale level unique to the interval in which they belong.

The result is a display wherein transition regions between the gray scale intervals are sharp and well-defined in the display. Gray scale density gradients produced from the tension induced in the tissue are visible in the display before the malignancy is observable, as the stress lines shown in FIG. 2. A bright red border 28 in this instance will appear in the mammogram illustrated in FIG. 2 to identify areas experiencing stress.

The comparison between right and left breast would obviously, as is known to clinicians and radiologists identify a potential malignancy. Additionally the display is advantageous in showing the stress patterns set up before the carcinoma is visibly evident.

By way of example, but not a limitation, each pixel value stored in the video buffer memory 17 is identified as belonging to an interval, and set to a gray scale value defined by the interval in accordance with the following formula:

If (PXvalue>236) PXvalue=PXvalue ^20×PXvalue−64 Else
PXvalue=PXvalue ^20×PXvalue.

The application of the foregoing value to the pixel results in four defined intervals of gray scale values for displaying a point on the mammogram, resulting in 15 new gray scale values which are repeated at different intervals.

The resulting table, omitting some of the new values, has the following configuration.

TABLE 1

| OLD | NEW | OLD | NEW | OLD | NEW | OLD | NEW | OLD | NEW |
|---|---|---|---|---|---|---|---|---|---|
| 0 to | 20 | 52 to | 124 | 104 to | 20 | 156 to | 44 | 208 to | 52 |
| 1 to | 20 | 53 to | 124 | 105 to | 20 | 157 to | 44 | 209 to | 52 |
| 2 to | 20 | 54 to | 124 | 106 to | 20 | 158 to | 44 | 210 to | 52 |
| 3 to | 20 | 55 to | 124 | 107 to | 20 | 159 to | 44 | 211 to | 52 |
| 4 to | 28 | 56 to | 116 | 108 to | 236 | 160 to | 20 | 212 to | 60 |
| 5 to | 28 | 57 to | 116 | 109 to | 236 | 161 to | 20 | 213 to | 60 |
| 6 to | 28 | 58 to | 116 | 110 to | 236 | 162 to | 20 | 214 to | 60 |
| 7 to | 28 | 59 to | 116 | 111 to | 236 | 163 to | 20 | 215 to | 60 |
| 8 to | 20 | 60 to | 108 | 112 to | 244 | 164 to | 28 | 216 to | 52 |
| 9 to | 20 | 62 to | 108 | 114 to | 244 | 166 to | 28 | 219 to | 52 |
| 10 to | 20 | 63 to | 108 | 115 to | 244 | 167 to | 28 | 218 to | 52 |
| 11 to | 20 | 63 to | 108 | 115 to | 244 | 167 to | 28 | 219 to | 52 |
| 12 to | 44 | 64 to | 20 | 116 to | 252 | 168 to | 20 | 220 to | 44 |
| . | | . | | . | | . | | . | |
| 24 to | 52 | 76 to | 44 | 128 to | 20 | 180 to | 124 | 232 to | 20 |
| 25 to | 52 | 77 to | 44 | 129 to | 20 | 181 to | 124 | 233 to | 20 |
| 26 to | 52 | 78 to | 44 | 130 to | 20 | 182 to | 124 | 234 to | 20 |
| 27 to | 52 | 79 to | 44 | 131 to | 20 | 183 to | 124 | 235 to | 20 |
| . | | . | | . | | . | | . | |
| 47 to | 108 | 99 to | 20 | 151 to | 60 | 203 to | 20 | 255 to | 172 |
| 48 to | 116 | 100 to | 28 | 152 to | 52 | 204 to | 44 | | |
| 49 to | 116 | 101 to | 28 | 153 to | 52 | 205 to | 44 | | |
| 50 to | 116 | 102 to | 28 | 154 to | 52 | 206 to | 44 | | |
| 51 to | 116 | 103 to | 28 | 155 to | 52 | 207 to | 44 | | |

Figure 3:
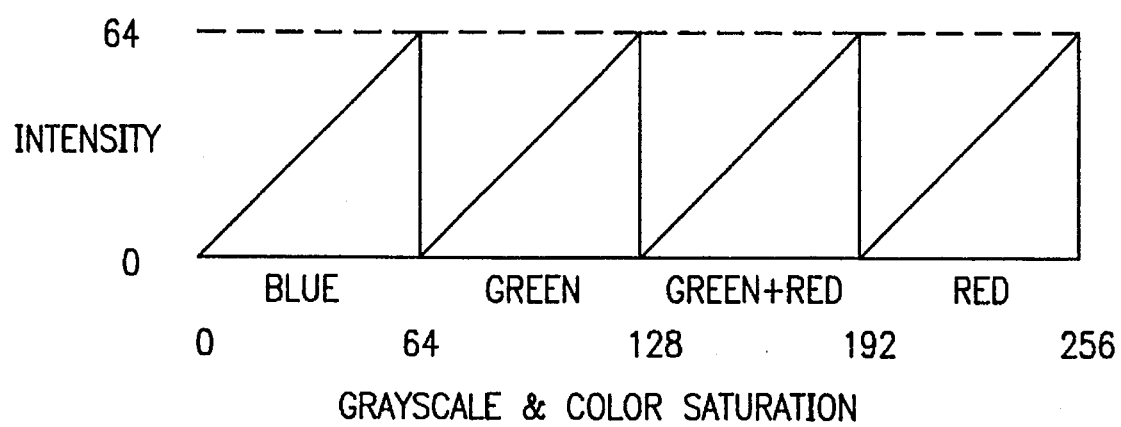
FIG. 3 illustrates the color assignment to each pixel gray scale interval.

The new values are then assigned a color by a color Look Up Table (LUT) contained in the video memory board 17 which is loaded by a table of values described in FIG. 3. The horizontal axis of FIG. 3 represents gray scale and color saturation, and the vertical axis represents color intensity. The Look Up Table is part of a video signal generator. The Look Up Table acts as a filter, between the computer and the display. During the display of an image, each old pixel value identifies a new value from Table 1 which addresses the Look Up Table. The Look Up Table translates the original gray scale value (0–255) to color intensity (0–63) level for each pixel which is displayed by RGB color monitor 28. Thus, each of the new gray scale levels of Table 1 produce a distinct color. A similar Look Up Table is provided as part of the video signal generator to generate a unique gray scale level for each pixel interval which can generate a video signal for display on monochrome monitor 27. Using the foregoing table and contents of the look-up table, a gray scale original value of 107 will first be converted to 20 and would display as dark blue. Likewise, an original gray scale LUT value of 108 (Table 1) would be converted to 236 represented on the horizontal axis of the figure which translates to a bright red (FIG. 3). The two gray scale values of 107 and 108 are adjacent to each other and are not discernible by the human eye until displayed with the new invention, in which case each is assigned a new, non-contiguous gray scale value, represented by distinctly different colors. These new gray scale color assignments make it possible to clearly identify gradients in tissue density which result from carcinoma-induced stress.

Each pixel in the preferred embodiment is displayed from a video signal which defines the pixel in terms of the colors of blue, green, yellow (green plus red) and red, read from the Look Up Table in accordance with FIG. 3.

The resulting display will show transitions of gray scale levels in very significant color bands. These color bands are further defined by bringing the transition from Blue to Green (at 64), Green to Green+Red to Red (at 192) down to black which highlights areas of high stress in the tissue.

Figure 4:
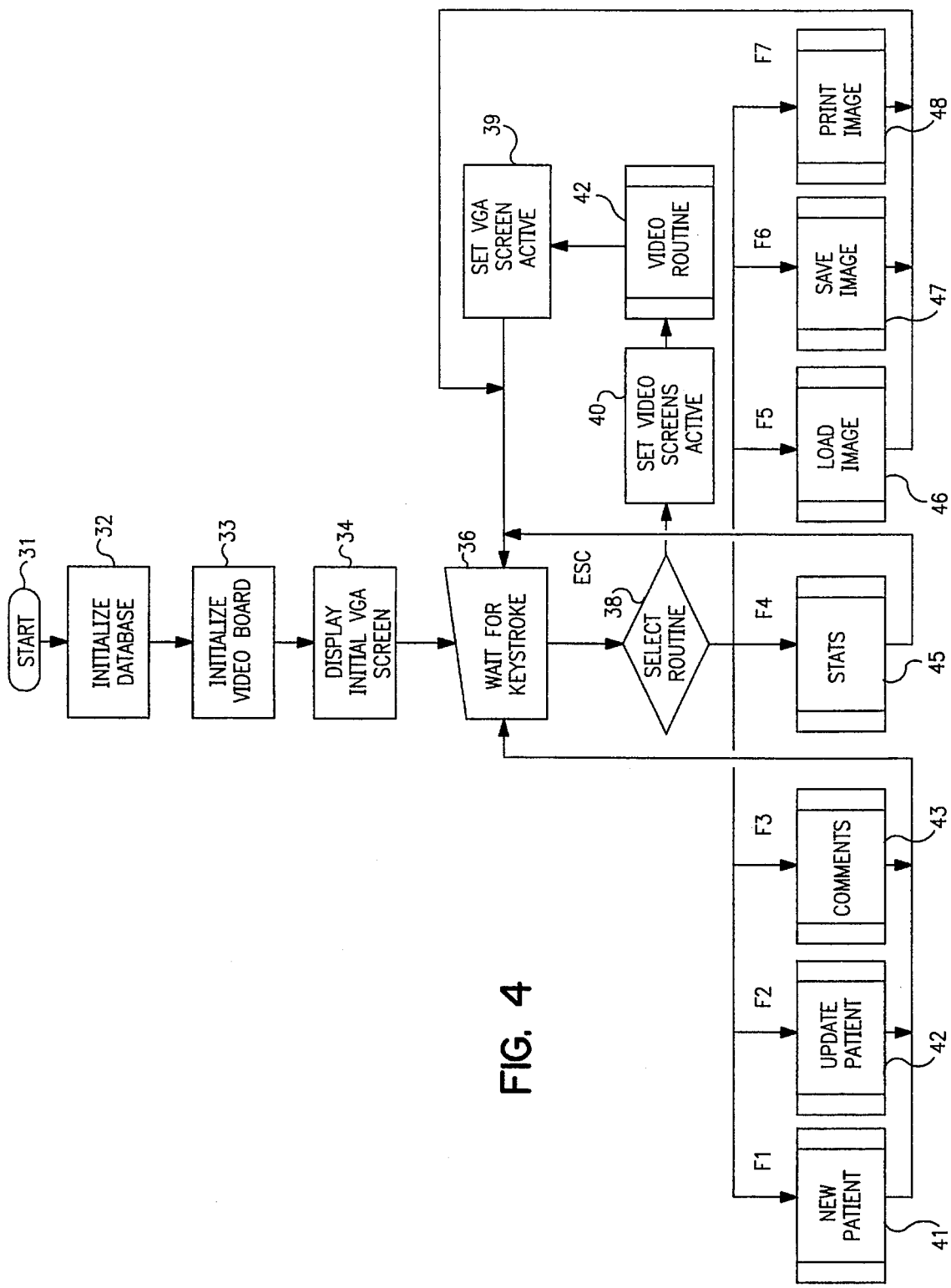
FIG. 4 illustrates the main computer routine executed by the computer of FIG. 1.
Figure 5:
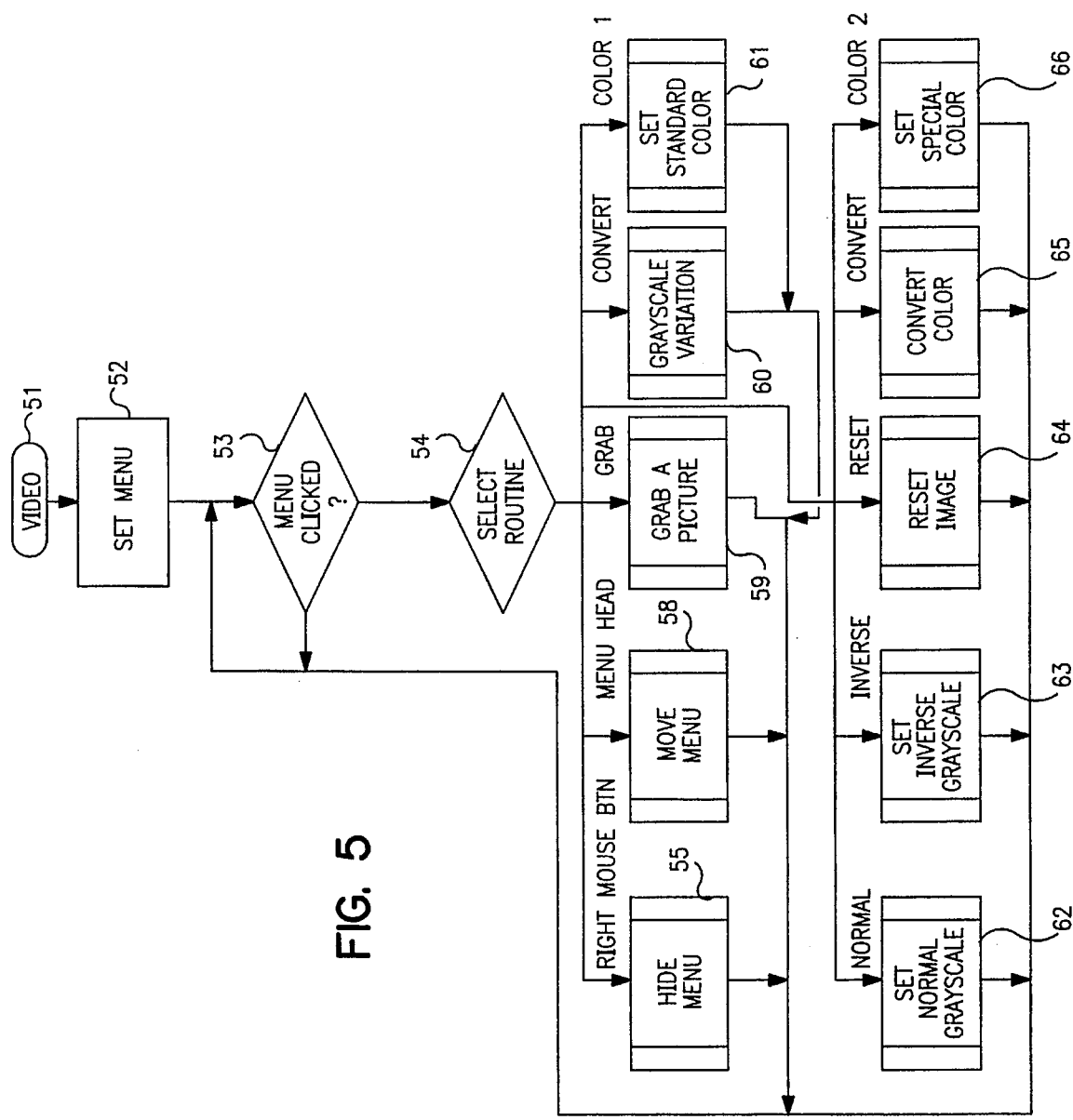
FIG. 5 illustrates the video routine executed by the computer of FIG. 1 to create the digitized image for display.

The arrangement of the software in computer 14 comprises a main routine, shown in FIG. 4 and a video routine shown in FIG. 5. The main routine of FIG. 4 is executed by computer 14, to permit the user to initialize the system, identify the patient and/or mammogram under examination, and otherwise create or update a record identifying the patient and/or mammogram under examination. This portion of the software is related to record keeping so that the clinician can memorialize the results of any mammogram analysis for future use.

The video routine of FIG. 5 relates to the specific steps for grabbing and digitizing the mammogram image, and creating the enhanced image in accordance with the preferred embodiment for display.

Turning now to FIG. 4, the main routine is illustrated with a start block of 31. The database is initialized in 32 by identifying the databases (patient and visit) used by this invention. In step 33 the video board 16 for acquiring and digitizing a scanned image from the camera 10 is initialized. The digitizer of the video board 16 goes through a self-check test under control of block 33, and the results are displayed to the operator on the VGA display 26.

The program is arranged so that the system is switched between the video routine 42 (shown in FIG. 5) and the main routine by selecting ESCAPE in step 38.

Function keys F1 through F7 initiate the various functions 41 through 48 which relates to record keeping by the clinician during analysis of the mammogram.

The operator is prompted from a menu displayed in step 34 to select one of the functions 41 through 48. The first of these functions F1 creates a new patient record. An initial menu is generated which is formatted as a blank record related to a particular patient. Alphanumeric data is entered via the keyboard 20 of the computer, to link the record to an image being analyzed. Data is entered identifying the patient, the date of analysis, etc.

The function 42 updates a patient's record, by permitting the record to be retrieved and additional data to be added to a previously entered record.

The clinician examining the mammograms in accordance with the present invention may insert comments in the record by exercising the function represented by 43, which permits text to be added to the record in a standard ASCII format. In addition to the comments the radiologist can enter statistical information by pressing F4, function 45.

F5, function 46 allows the clinician to load from the computer hard disk a previously saved image, to the computer display memory.

F6, function 47 on the other hand allows the clinician to save an image to the hard disk of computer 14. This image could have previously been acquired by the video routines in function 42 or it could have been loaded by function 46.

F7, function 48 permits the clinician to print the hard copy of the image acquired by video function 42 or loaded by function 46 in the video memory board 17.

Any of the functions 41 through 48 will end by returning to standby mode waiting for the next key stroke in function 36. If this key stroke is the escape key, the system will switch to video mode described in FIG. 5.

Referring to FIG. 5, there is shown in detail the video routine which will grab the digitized image from the video board 16 analog to digital converter, store it in the video memory and present it for display to the user. The start of the video routine is denoted by 51. A menu is produced in step 52, which provides the user with the options to execute one of the functions 58 through 66. The menu is fully displayed and the user makes a selection by pointing to his preferred menu selection with mouse 21 and a subsequent selection of a menu item is detected in decision block 53 and 54.

The blocks 55 and 58 through 66 represent the following functions:

| | |
|---|---|
| 55 | Hide the menu |
| 58 | Move the menu |
| 59 | Grab picture |
| 60 | Gray scale variation |
| 61 | Set standard color |
| 62 | Set normal gray scale |
| 63 | Set inverse gray scale |
| 64 | Reset image |
| 65 | Convert color |
| 66 | Set special color |

The analysis of the image begins with the GRAB PICTURE function 59. When the user moves the cursor of the displayed menu to the GRAB PICTURE line of the menu displayed on the monochrome monitor 27 or color monitor 28 and clicks the mouse a command is provided to the camera 10 of FIG. 1, to open the camera shutter 10, to provide a live picture on the monochrome screen 27 and color screen 28 and the picture will remain live for the operator to adjust field of view, focus and brightness, until one of the 2 buttons on mouse 21 is clicked. At this point the picture is digitized and stored in video memory board 17 and on the computer hard disk at a dedicated address. Function 59 now displays the menu and returns to function 53.

Function 65, CONVERT COLOR, will apply the previously defined formula which created Table 1 to each pixel to create each new pixel gray scale value. Function 65 then returns the user to the menu selection 53.

Function 66, SET SPECIAL COLOR, is now selected. This function will convert the captured image to the color described in FIG. 3 by loading the Look Up Table with the table of color values shown in FIG. 3. A video signal is generated by addressing the Look Up Table with a discreet gray scale level obtained from CONVERT COLOR corresponding to the new gray scale level for each pixel. A video signal generator on the video memory board 17 creates a video signal from the output color information read from the Look Up Table. The color monitor will display the image produced from the Look Up Table.

Function 61, SET STANDARD COLOR, is used to reset the image to original start-up colors as set by Function 33. Function 61 then returns the user to the menu selection 53.

The clinician, viewing the displayed color image of FIG. 2 can identify the areas of high stress by looking at the color boundaries and detect the presence of a suspicious lesion in the tissue.

The RESET function 64, will take the operator back to the display of the initial image which was originally stored in computer video memory 17 before any image enhancements were effected. Thus, should the operator have moved into either a GRAY SCALE VARIATION 60 or CONVERT COLOR 65, and wish to return to the original image the RESET function may be elected. The previously stored image on the computer hard disk is retrieved and stored in the video memory 17.

The NORMAL FUNCTION 62 will display black and white mammograms in the correct polarity on the monochrome monitor 27. The INVERSE function 63 will permit the user to create a negative image, wherein black becomes white and white becomes black, enabling the clinician to make other judgements regarding the displayed mammograms.

If in the color image above currently one the RGB screen 28 indicates a stress pattern or a suspicious density, Function 60, Gray scale variation is selected to vary the gray scale between normal and inverse images. Gray scale variation can be used to produce a modified gray scale which will highlight gray scale density gradient. This in combination with zooming-in the camera to the indicated density (using zoom button on camera 10) allows the clinician to bring out micro-calcifications and density changes, such as spicules, that might exist hidden to the human eye on the monochrome monitor 27.

Function 58, Move menu, permits the operator to move the menu text to another part of the screen thus allowing him to view parts of the mammogram that were covered previously.

Function 55 is an exception to the other functions. Function 55 is selected by clicking the right mouse button without pointing to any item. This function will simply remove the menu from the screen. Clicking any mouse button, left or right, after removing the menu will return the menu to the screen.

Thus, there is described the system which will permit the analysis of mammograms, to locate suspicious areas of stress within the tissue of a patient. The stress lines produced from the analysis will localize earlier detection of malignancies, so that the appropriate diagnosis and treatment may be made at an early stage in the development of disease.

The invention has been described with respect to one embodiment of the invention a system for analyzing X-ray images. Those skilled in the art will recognize yet other variations of the invention by the claims which follow.

What is claimed is:

1. An apparatus for analyzing a mammogram to identify carcinoma-induced stress in tissue comprising:

a camera for creating a scanned video image from said mammogram;

a video signal digitizing means for creating a digitized image from said scanned video image comprising an array of pixels, each pixel defining a gray scale level for a point on said mammogram representing a tissue density recorded on said mammogram;

a computer including a video memory for storing said array of pixels, said computer being programmed to:

divide the array of pixels into discrete separate groups of pixels forming contiguous ranges of gray scales, each group including pixels having a gray scale value within a range unique to said group;

assigning a single pixel value to each pixel of each group said single pixel value selected so that adjacent groups comprise non-contiguous groups of a single pixel value;

addressing a look-up with each assigned pixel value, to produce a plurality of pixel colors having a saturation and intensity level defined by each assigned pixel value whereby each color includes a range of intensity levels, said intensity level increasing from a black level to a maximum level for increasing assigned pixel values whereby further increases in an assigned pixel value produces another color which increases in intensity level for increasing assigned pixel values; and a display for displaying an image comprising said pixel colors, wherein pixels lying within each of said groups have the same display value, said image having discrete boundaries defined by non-contiguous pixel values representing a tissue density gradient produced by carcinoma-induced stress.

2. The apparatus according to claim 1 wherein said Look Up Table defines 64 color intensity levels for 256 assigned gray scale values.

3. The apparatus according to claim 1 further comprising means for varying the gray scale of said stored digitized image pixels.

4. A method for detecting stress induced in human tissue during the early stages of a malignant condition comprising:

forming a digital image of said tissue comprising a frame of pixels having a gray scale value representing a tissue density;

translating each pixel gray scale into one of a limited number of discrete gray scale values, so that pixels having a gray scale value which lies within a small gray scale interval have the same gray scale values, and adjacent intervals have non-contiguous gray scale values; and, displaying each of said discrete gray scale values at each pixel location, as a distinct color from a look-up table which translates each translated pixel gray scale value into one of a plurality of distinct colors, each color including a range of intensity values, said look up table defining an intensity level for each display color based on a translated pixel gray scale value, said intensity level increasing from a minimum intensity level to a maximum intensity level with increasing translated pixel gray scale values until a boundary is reached with another color, whereby areas of substantially constant tissue density are represented as contours having the same display value, and tissue areas of high stress produce several adjacent bands of different displayed values of a distinctive shape.

5. The method according to claim 4, wherein said boundary between colors is defined by a transition from said maximum intensity level to a black level.

6. The method for detecting stress induced in human tissue during the early stages of a malignant condition of claim 4 wherein said step of forming a digital image comprises:

illuminating a mammogram with a light box;

scanning an image produced by said mammogram to produce a scanned video image; and digitizing said scanned video image.

* * * * *